United States Patent

Szekely et al.

[11] 4,248,888
[45] Feb. 3, 1981

[54] CHEMICAL COMPOUNDS

[75] Inventors: István Szekely, Szentendre; Marianna Lovasz, nee Gaspar, Budapest; Gabor Kovács, Budapest; Rudolf Soos, Budapest; Lajos Nagy, Szentendre; Bela Köszegi, Budapest, all of Hungary

[73] Assignee: Chinoin Gyógyszer és Vegyészeti Termékek Gyára R.T., Budapest, Hungary

[21] Appl. No.: 13,069

[22] Filed: Feb. 21, 1979

[30] Foreign Application Priority Data

Feb. 23, 1978 [HU] Hungary .................. CI-1813

[51] Int. Cl.³ .................. C07C 69/747; C07C 69/743; A01N 53/00
[52] U.S. Cl. .................. 424/306; 424/305; 560/124; 260/346.22
[58] Field of Search .................. 560/124; 424/305, 306

[56] References Cited

U.S. PATENT DOCUMENTS

| | | | |
|---|---|---|---|
| 2,603,652 | 7/1952 | Schechter | 560/124 |
| 2,661,374 | 12/1954 | Schechter | 560/124 |
| 2,768,965 | 10/1956 | Stansbury | 560/124 |
| 2,891,888 | 6/1959 | Guest | 560/124 |
| 2,891,889 | 6/1959 | Haynes | 560/124 |
| 3,009,946 | 11/1961 | Takei | 560/124 |
| 3,282,985 | 11/1966 | Matsui | 560/124 |
| 3,284,486 | 11/1966 | Matsui | 560/124 |
| 3,636,059 | 1/1972 | Matsui | 560/124 |
| 3,998,868 | 12/1976 | Mizutani | 560/124 |
| 4,024,163 | 5/1977 | Elliott | 560/124 |

OTHER PUBLICATIONS

Tomoskozi, Tetrahedron Letters, 50 p. 4639–4642, (1976).
Szekely, Tetrahedron Letters, pp. 4503–4506 (1976).
Tomoskozi, Tetrahedron Letters, pp. 4639–4642 (1976).

Primary Examiner—Natalie Trousof
Assistant Examiner—Michael Shippen
Attorney, Agent, or Firm—Karl F. Ross

[57] ABSTRACT

Insecticidal compounds of the formula:

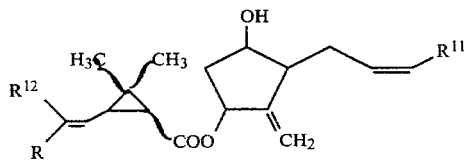

wherein
$R^{11}$ is a straight or branched chain lower alkyl or 1-alkenyl or hydrogen;
R and $R^{12}$ are the same or different and are hydrogen, halogen, or straight or branched chained lower alkyl, or one of the moieties R and $R^{12}$ is lower alkoxycarbonyl; the bonds represent α- and/or β-configuration and the — bonds represent β-configuration.

7 Claims, No Drawings

CHEMICAL COMPOUNDS

This invention relates to new chemical compounds, a process for their preparation and insecticidal compositions containing the same.

According to a feature of the present invention there are provided new optically active and racemic compounds of the formula I

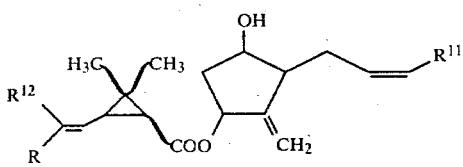

wherein
$R^{11}$ is straight or branched chained lower alkyl or 1-alkenyl or hydrogen;
R and $R^{12}$ are the same or different and are hydrogen, halogen, straight or branched chained lower alkyl or one of the moieties R and $R^{12}$ is lower alkoxycarbonyl;
the ∼ bonds represent α- and/or β-configuration and the — bonds represent β-configuration.

The new compounds of the formula I possess insecticidal properties and are useful intermediates in the preparation of insecticidal pyrethroides.

The term "straight or branched chained lower alkyl" relates to alkyl groups having 1 to 6, preferably 1 to 4 carbon atoms (such as methyl, ethyl, n-propyl, isopropyl and n-butyl). The term "halogen" encompasses the fluorine, bromine, chlorine and iodine atoms. The term "1-alkenyl" relates to 1-alkenyl groups having 2 to 6 carbon atoms (e.g. vinyl). The alkoxy moiety of the lower alkoxycarbonyl group has 1 to 6, preferably 1 to 4 carbon atoms (e.g. methoxycarbonyl and ethoxycarbonyl).

R and $R^{12}$ preferably stand for methyl.

Particularly preferred representatives of the compounds of the formula I are the following derivatives:
1β-hydroxy-2β-(but-2-cis-enyl)-3-methylene-cyclopentane-4β-yl-(+)-trans-chrysanthemate;
1β-hydroxy-2β-(pent-2-cis-enyl)-3-methylene-cyclopentane-4β-yl-(+)-trans-chrysanthemate;
1β-hydroxy-2β-(prop-2-enyl)-3-methylene-cyclopentane-4β-yl-(+)-trans-chrysanthemate;
1β-hydroxy-2β-(but-2-cis-enyl)-3-methylene-cyclopentane-4β-yl-[2,2-dimethyl-3S-(2,2-dichloro-vinyl)-cyclopropane-1-carboxylate];
1β-hydroxy-2β-(but-2-cis-enyl)-3-methylene-cyclopentane-4β-yl-[2,2-dimethyl-3-(2,2-difluoro-vinyl)-cyclopropane-1-carboxylate].

The compounds of the formula I may be present either in optically active or racemic form. The invention covers the two optically active and the racemic forms as well.

According to a further feature of the present invention there is provided a process for the preparation of the compounds of the formula I which comprises (a) reacting an optically active or racemic 2-substituted-1,4-dihydroxy-3-methylene-cyclopentane derivative of the formula II

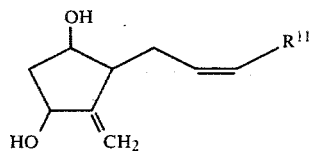

(wherein $R^{11}$ and ∼ have the same meanings stated above) with a chrysanthemic acid derivative of the formula III

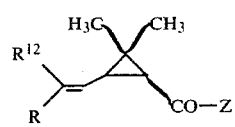

(wherein R, $R^{12}$, ∼ and — have the same meanings stated above and Z stands for halogen, mesyl, tosyl, imidazolyl or a group of the formula —O—CO—Q, in which Q is a straight or branched chained optionally halogeno-substituted alkyl or alkoxy group or an aryl, aryloxy, aralkyl or aralkoxy group or Z stands for a group of the formula IV

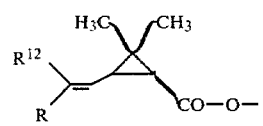

in which R, $R^{12}$, ∼ and — are as stated above) in an aprotic inert organic solvent in the presence of a base; or (b) reacting a 4α-halogenomethyl-2-hydroxy-3,3aα,4,5,6,6aα-hexahydro-2H-cyclopentano[b]furan-5β-O-yl-chrysanthemate derivative of the formula V

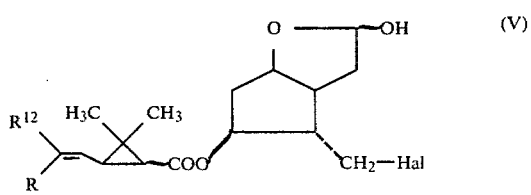

(wherein R, $R^{12}$, ∼ and — are as stated above, while the bond — represents α-configuration and Hal is halogen) in an inert aprotic organic solvent with 2.1-n moles of a phosphorane of the formula VI

$\phi_3P{=}CH{-}R^{11}$ (VI)

(wherein φ is a phenyl group optionally substituted by lower alkyl or halogen and $R^{11}$ is as stated above) and with n moles of a tertiary amine base (wherein n is an optional number between 0 and 1); or (c) reacting a 4-methylene-2-hydroxy-3,3aα,4,5,6,6aα-hexahydro-2H-cyclopentano[b]furan-5β-O-yl-chrysanthemate derivative of the formula VII

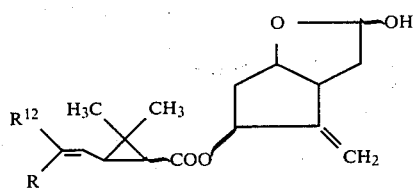

(VII)

(wherein R, $R^{12}$, ~ and — are as stated above) in an inert aprotic organic solvent with a phosphorane of the formula VI (wherein φ and $R^{11}$ are as stated above); or (d) reacting a 4α-arylthiomethyl-2-hydroxy-3,3aα,4,5,6,6aα-hexahydro-2H-cyclopentano[b]furan-5β-O-yl-chrysanthemate derivative of the formula VIII

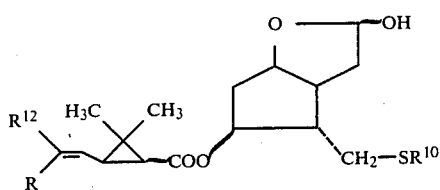

(VIII)

(wherein R, $R^{12}$, —, ~ and - - - are as stated above and $R^{10}$ is a phenyl group optionally mono- or polysubstituted by halogen, lower alkyl, lower alkoxy, phenyl, nitro and/or di-(lower)-alkyl-amino) with a phosphorane of the general formula VI (wherein φ and $R^{11}$ are as stated above) in an inert aprotic organic solvent, and thereafter oxidizing the chrysanthemic ester derivative of the formula X

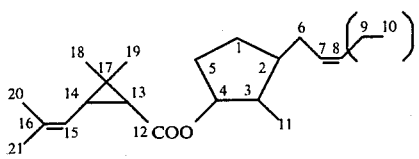

(X)

thus obtained (wherein R, $R^{11}$, $R^{12}$, $R^{10}$, ~, - - - and — are as stated above) into the corresponding sulfoxide derivative and splitting the said compound by heating or treatment with a tertiary amine.

In the process of the present invention the aprotic inert organic solvent is preferably an aromatic hydrocarbon (e.g. benzene, toluene etc.), an ether type solvent (such as tetrahydrofuran, dioxane), a halogenated hydrocarbon (e.g. methylene chloride or dichloroethane). An acid amide type solvent (e.g. dimethylformamide) may be used as well. In reaction variant (b) the solvent may be partly or completely replaced by the tertiary amine base. Here one may proceed particularly preferably by using 1,5-diaza-bicyclo[4,3,0]non-5-en (referred to in the Examples as DBN) or 1,5-diaz-bicyclo-[5,4,0]undec-5-en (referred to in the Examples as DBU).

In reaction variant (a) inorganic or organic bases may be used. One preferably uses an organic tertiary amine base such as triethylamine, pyridine, imidazole, DBN or DBU. In symbol Q the aryl moiety of the aryl, aryloxy, aralkyl or aralkoxy groups may be an aromatic radical having 6-10 carbon atoms (e.g. phenyl or nahthyl which may be optionally substituted but which is preferably an unsubstituted phenyl radical). In the definition of symbol Q the alkyl moiety of the alkyl, alkoxy, aralkyl or arylkoxy group may contain 1-10, preferably 1-4 carbon atoms and may be a straight or branched chained alkyl group.

Reaction variant (a) may be preferably carried out by dissolving the activated acid derivative of the formula III in an inert aprotic organic solvent, adding a suitable base (e.g. a tertiary amine) to the solution and thereafter adding the solution of the cyclopentane starting material of the formula II formed with an aprotic inert organic solvent.

One may also proceed preferably by forming in situ the activated chrysanthemic acid derivative of the formula III in an aprotic inert organic solvent and thereafter adding the cyclopentane derivative of the formula II to be acylated. The in situ formation of the starting materials of the formula III is particularly advantageous if Z is mesyl, tosyl, imidazolyl or —O—CO—Q. The reaction temperature may vary between wide ranges; one may work preferably at 0° to 80° C. Under such circumstances the reaction takes place within 1 to 60 hours depending on the definition of symbol Z. The compound of the formula I thus obtained can be recovered by known methods, preferably by extraction and can be purified by means of chromatography.

According to reaction variants (b), (c) and (d) a Wittig reaction is carried out in an inert aprotic organic solvent. The reaction temperature may vary between wide ranges (e.g. 5° to 80° C., preferably 5° to 20° C.). One preferably proceeds by adding the solution of the starting material of the formula V, VII or VIII to the suspension or solution of the phosphorane of the formula VI formed with an inert aprotic organic solvent.

The phosphoranes of the formula VI can be prepared by known methods. Thus they can be prepared by reacting the corresponding triphenyl-alkyl-phosphonium salt with a conjugated base (e.g. an alkali alcoholate, alkali amide, butyl lithium, alkali-methylsulfinyl-methide) in an anhydrous solvent (e.g. in the aprotic solvents enumerated above) or liquid ammonia.

In the above reactions the reaction mixture containing the phosphorane may be used or the phosphorane may also be isolated and used in salt-free form. The process is preferably carried out by forming the phosphorane in liquid ammonia, then allowing the ammonia to evaporate, extracting the residue with an inert aprotic organic solvent disclosed above and filtering the solution. The salt-free phosphorane solution may be advantageously used for the preparation of compounds of the formula I containing a cis double bond in the side chain.

In reaction variant (d) chrysanthemic ester derivatives of the formula IX

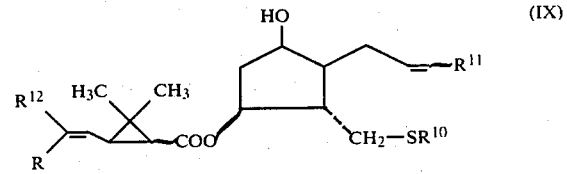

(IX)

are obtained, the arylthiomethyl side chain of these compounds is oxidized into a sulfoxide group and the derivatives thus obtained are heated or treated with a tertiary amine base to remove the sulfoxide group. Oxidation is preferably carried out with a peracid or salts thereof such as m-chloroperbenzoic acid or sodium periodate. This reaction can be carried out in aqueous solution or a mixture of water and an organic solvent.

The sulfoxide derivative thus obtained may be split by heating the reaction mixture to a temperature of 60° to 100° C. or treating the same with one of the tertiary amine bases enumerated above.

The 2-substituted 1,4-dihydroxy-3-methylene-cyclopentane starting materials of the formula II can be prepared in a known manner [Tetrahedron Letters 50, 4639-42 (1976)] by subjecting 3,3aα,4,5,6,6aα-hexahydro-2-oxo-4α-hydroxymethyl-5β-hydroxy-2H-cyclopentano[b]furan to selective halogenation of the hydroxymethyl group, reducing the oxo group of the 4α-halogenomethyl derivative thus obtained, alkylating the lactol derivative thus formed with a phosphorane of the formula VI and splitting off hydrogen halide from the compound thus obtained.

The starting materials of the formula V can be prepared by acylating a 4α-halogenomethyl derivative mentioned above with a chrysanthemic acid derivative of the formula III and reducing the lactone group in the ester thus obtained to lactol group for instance with diisobutyl aluminum hydride.

The starting materials of the formula VII can be prepared from 3,3aα,4,5,6,6aα-hexahydro-2-oxo-4α-hydroxymethyl-5β-hydroxy-2H-cyclopentano[b]furan e.g. by subjecting this compound to selective halogenation and dehydrohalogenation in a tertiary amine and acylating the 4-methylene derivative thus obtained with a chrysanthemic acid derivative of the formula III and reducing the compound thus obtained as described above.

The starting materials of the formula VIII can be prepared by reacting the 4α-halomethyl derivative with an alkali metal salt of a thiophenol of the formula HS-$R^{10}$ acylating the 4α-arylthiomethyl derivative thus obtained with a chrysanthemic acid derivative of the formula III and reducing the lactone group in the compound thus obtained into a lactol group in a manner described above.

The compounds of the formula I thus obtained can be converted into pyrethroides having insecticidal effect by means of oxidative rearrangement.

The compounds of the formula I possess insecticidal properties.

According to a further feature of the present invention there are provided insecticidal compositions comprising as active ingredient a compound of the formula I in admixture with suitable inert solid, liquid or gaseous carriers or diluents and if desired additives such as surface active agents.

The composition can be finished in forms and by methods generally used in the manufacture of insecticides. Thus they can formulated as dusting powders, granules, wettable or dispersible or soluble powder mixtures or granules, spray, solutions, emulsions or as aerosols. The carriers can be solid (e.g. organic or inorganic lours, China clay, kaolin, attapulgus clay, fuller's earth etc.), liquid (e.g. water), organic solvents (such as ketones, e.g. acetone; hydrocarbons, e.g. benzene, toluene; halogenated hydrocarbons etc.) or gaseous diluents (e.g. carbon dioxide or halogenated hydrocarbons or mixtures thereof).

The compositions can contain surfactants too. These surface active agents may be those generally used in the manufacture of insecticides and can of cationic, anionic or non-ionic character.

The insecticidal activity of the compounds of the formula I is demonstrated by test results obtained on Musca domestica and Blatta germanica; dosage 2–5 μg/insect; method: topical exposition techniques. The results are summarized in the following Table I (the symbols relate to the formula I):

TABLE I

| R | $R^{12}$ | $R^{11}$ | $KD_{50}$(minutes) | Mortality (in %) after 24 hours |
|---|---|---|---|---|
| $CH_3$ | $CH_3$ | $CH_3$ | 40 | 100 |
| $CH_3$ | $CH_3$ | H | 45 | 100 |
| $CH_3$ | $CH_3$ | $CH_2=CH-$ | 20 | 100 |
| Cl | Cl | $CH_3$ | 50 | 60 |
| Br | Br | $CH_3$ | 50 | 65 |
| F | F | $CH_3$ | 25 | 50 |

Further details of the present invention are to be found in the Examples without limiting our invention to the Examples.

EXAMPLE 1

2.1 g. of 1β,4β-dihydroxy-2β-(but-2-cis-enyl)-3-methylene-cyclopentane and 4 ml of anhydrous benzene are mixed and cooled to 10° C., whereupon 1.2 ml. of pyridine are added and at 10° to 15° C. a solution of 2.43 g. of (+)-trans-chrysanthemic acid chloride in 20 ml of benzene is added dropwise. The reaction mixture is stirred at room temperature for 40 hours. The reaction is followed by means of thin layer chromatography (silica gel; eluting solvent 4:1 mixture of petroleum ether and ethyl acetate).

The reaction mixture is diluted with benzene and washed with 1 N hydrochloric acid. The acidic phase is extracted with benzene, the organic layers are combined, extracted with a 5% aqueous sodium hydrogen carbonate solution, dried over anhydrous sodium sulfate and benzene is distilled off. 3.5 g. of crude 1β-hydroxy-2β-(but-2-cis-enyl)-3-methylene-cyclopentane-4β-yl-(+)-trans-chrysanthemate are obtained.

The product is subjected to chromatography on silica gel. 2.83 g. of the pure compound are obtained. Yield: 71.3%.

$R_f=0.53$ (on a "G Merck" silica gel plate; eluting solvent 4:1 mixture of petroleum ether and ethyl acetate).

IR (film): $v_{max}=3500$, 2940, 1725, 1430, 1380, 1180, 1150, 1110 and 850 cm$^{-1}$.

The same results are obtained if pyridine is replaced by an equimolar amount of triethylamine.

NMR spectrum (in CDCl$_3$): δ=4.2 (m, 1H, H−1), 4.92 (m, 1H, H-4), 5.4–5.7 (m, 3H, H-7, H-8, H-15), 5.2 and 5.34 (m, 2H, H-11), 1.12 and 1.27 (s and s, 3H and 3H, H-18, H-19), 1.71 (s, 6H, H-20, H-21).

(The numbers in parentheses means the number of the carbon atom to which the proton is linked; the numbering is shown on formula X).

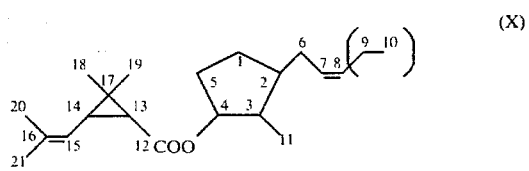

(X)

EXAMPLE 2

0.358 g. of (+)-trans-chrysanthemic acid are dissolved in 3 ml. of anhydrous benzene, whereupon 2.94 ml. of triethylamine are added. To the suspension 272 mg. (226 μl) of benzyl-chloro-formiate are added dropwise. To the suspension formed a solution of 270.6 mg. of 1β,4β-dihydroxy-2β-(but-2-cis-enyl)-3-methylene-cyclopentane and 2 ml. of benzene is added. The reaction mixture is stirred at 70° C. for 16 hours. The reaction is followed by thin layer chromatography (silica gel plate; elution agent 4:1 mixture of petroleum ether and ethyl acetate).

The reaction mixture is treated according to Example 1. 320 g. of crude and 158 mg. of pure 1β-hydroxy-2β-(but-2-cis-enyl)-3-methylene-cyclopentane-4β-yl-(+)-trans-chrysanthemate are obtained. Yield: 31%.

The physico-chemical data of this product correspond to Example 1.

EXAMPLE 3

The process according to Example 2 is carried out except that the benzyl-chloro-formiate is replaced by a solution of 298.8 mg. of (+)-trans-chrysanthemic acid chloride in 1 ml. of benzene, which is added to the solution of (+)-trans-chrysanthemic acid, triethylamine and benzene. 137.6 g. of 1β-hydroxy-2β-(but-2-cis-enyl)-3-methylene-cyclopentane-4β-yl(+)-trans-chrysanthemate are obtained. Yield: 27%. The physical data correspond to the data obtained for the compound of Example 1.

EXAMPLE 4

The process according to Example 2 is carried out except that instead of benzyl-chloro-formiate 182.1 g. of methane-sulfonyl-chloride dissolved in 1 ml. of benzene are added to the solution of (+)-trans-chrysanthemic acid, benzene and triethylamine. 208.9 g. of 1β-hydroxy-2β-(but-2-cis-enyl)-3-methylene-cyclopentane-4β-yl-(+)-trans-chrysanthemate are obtained. Yield: 41%. The product is identical with the product of Example 1.

Similar results are obtained when replacing methane sulfonyl chloride by p-toluene-sulfonyl chloride.

EXAMPLE 5

The process according to Example 2 is carried out except that instead of benzyl chloroformiate 191.8 mg. of pivaloyl chloride are added to the solution of (+)-trans-chrysanthemic acid, triethylamine and benzene. 127.4 mg. (25%) of 1β-hydroxy-2β-(but-2-cis-enyl)-3-methylenecyclopentane-4β-yl-(+)-trans-chrysanthemate are obtained. The product is identical with the product of Example 1.

EXAMPLE 6

The process according to Example 1 is carried out except that 2.1 g. of 1β,4β-dihydroxy-2β-(but-2-cis-enyl)-3-methylene-cyclopentane are replaced by 2.26 g. of 1β,4β-dihydroxy-2β-(pent-2-cis-enyl)-3-methylene-cyclopentane. Thus 2.9 g. (70.5%) of 1β-hydroxy-2β-(pent-2-cis-enyl)-3-methylene-cyclopentane-4β-yl-(+)-trans-chrysanthemate are obtained.

$R_f$=0.55 (60 $F_{254}$ Merck silica-gel plate; eluting solvent 4:1 mixture of petroleum ether and ethyl acetate).

$M^1$ NMR (CDCl$_3$) δ: 4.2 (m, 1H, H-1), 4.92 (m, 1H, H-4), 5.4–5.7 (m, 3H, H-7, H-8, H-15), 0.99 (t, 3H, H-10), 5.2 and 5.34 (m, 2H, H-11); 1.12 and 1.27 (s and s, 3H and 3H, H-18 and H-19), 1.71 (s, 6H, H-20, H-21).

C-13 NMR spectrum δ ppm: C-1 72.30; C-2 49.19; C-3 151.7; C-4 74.48; C-5 40.30; C-6 24.99; C-7 126.84; C-8 121.14; C-9 20.68; C-10 14-26; C-11 111.36; C-12 172.17; C-13 34.99; C-14 32.80; C-15 133.06; C-16 135.52; C-17 28.73; C-18 20.44; C-19 22.21; C-20 25.50; C-21 18.47.

EXAMPLE 7

The process according to Example 1 is carried out except that 2.1 g. of 1β,4β-dihydroxy-2-(but-2-cis-enyl)-3-methylene-cyclopentane are replaced by 1.91 g. of 1β,4β-dihydroxy-2β-(prop-2-enyl)-3-methylene-cyclopentane. 2.87 g. (76%) of 1β-hydroxy-2β-(prop-2-enyl)-3-methylene-cyclopentane-4β-yl-(+)-trans-chrysanthemate are obtained.

$R_f$=0.52 (60 $F_{254}$ Merck silica-gel plate, eluting agent 4:1 mixture of petroleum ether and ethyl acetate).

NMR spectrum (CDCl$_3$) δ: 4.22 (m, 1H, H-1); 4.95 (m, 1H, H-4); 5.38–5.72 (m, 4H, H-7, H-8 H-8, H-15), 5.2 and 5.34 (m, 2H, H-11), 1.12 and 1.26 (s and s, 3H and 3H, H-18 and H-19), 1.71 (s, 6H, H-20 and H-21).

EXAMPLE 8

The process according to Example 2 is carried out except that in the place of benzyl chloro formiate a solution of 334 mg. of trifluoro acetic anhydride in 1 ml. of benzene is added to the solution of (+)-trans-chrysanthemic acid, benzene and triethylamine. 336.4 mg. (66%) of 1β-hydroxy-2β-(but-2-cis-enyl)-3-methylene-cyclopentane-4β-yl-(+)-trans-chrysanthemate are obtained. The product is identical with that of Example 1.

EXAMPLE 9

The process according to Example 2 is carried out except that at first 181.3 g. of trifluoro acetic acid are dissolved in 1 ml. of benzene, whereupon 2.94 ml. of triethylamine and then 397 mg. of (+)-trans-chrysanthemic acid chloride are added. Thus 219.2 mg. (43%) of 1β-hydroxy-2β-(but-2-cis-enyl)-3-methylene-cyclopentane-4β-yl-(+)-trans-chrysanthemate are obtained. The product is identical with that of Example 1.

EXAMPLE 10

The process according to Example 9 is carried out except that 181.3 g. of trifluoroacetic acid are replaced by 289.9 g. of imidazole. Thus 214.1 mg. of 1β-hydroxy-2β-(but-2-cis-enyl)-3-methylene-cyclopentane-4β-yl-(+)-trans-chrysanthemate are obtained. Yield: 42%. The product is identical with the compound prepared according to Example 1.

EXAMPLE 11

6.1 g. of 3,3aα,4,5,6,6aα-hexanhydro-2-hydroxy-4α-bromomethyl-5β-O-yl-(+)-trans-chrysanthemate and 20 ml. of anhydrous benzene are reacted in nitrogen atmosphere. The solution is cooled to 10° to 15° C. whereupon 36 ml. of a molar triphenyl-ethylidene-phosphorane solution is added under stirring (benzene solution, containing 36 millimoles of phosphorane). The reaction is followed by thin layer chromatography (G. Merck Art. No. 1719 silica gel plate, eluting agent 4:1 mixture of petroleum ether and ethyl acetate). After about one and a half hours the reaction mixture is treated as described in Example 1.

The crude product is subjected to chromatography on silica gel. The fractions corresponding to an $R_f$ value of 0.66 (in a 3:1 mixture of petroleum ether and ethyl acetate) are collected. 4.74 g. (94.7%) of 1β-hydroxy-2β-(but-2-cis-enyl)-3-methylene-cyclopentane-4β-yl-(+)-trans-chrysanthemate are obtained.

IR (film): $\delta_{max}$=3490, 2945, 1725, 1430, 1175, 1150, 1110 and 850 cm$^{-1}$.

NMR (CDCl$_3$) δ=4.2 (m, 1H), 4.92 (m, 1H), 5.4–5.7 (m, 3H), 5.2 and 5.3 (m, 2H, exo methylene), 1.12 and 1.27 (s and s, 3H and 3H), 1.71 (s, 6H).

In a manner analogous to the above process the following compounds are prepared:

1β-hydroxy-2β-(pent-2-cis-enyl)-3-methylene-cyclopentane-4β-yl-(+)-trans-chrysanthemate, $R_f$=0.55 (4:1 mixture of petroleum ether and ethyl acetate.

1β-hydroxy-2β-(pent-cis-2,4-dienyl)-3-methylene-cyclopentane-4β-yl-(+)-trans-chrysanthemate ($R_f$=0.59; 3:1 mixture of petroleum ether and ethyl acetate);

1β-hydroxy-2β-(prop-2-enyl)-3-methylene-cyclopentane-4β-yl-(+)-trans-chrysanthemate ($R_f$=0.52, in a 4:1 mixture of petroleum ether and ethyl acetate);

1β-hydroxy-2β-(but-2-cis-enyl)-3-methylene-cyclopentane-4β-yl-[2,2-dimethyl-3S-(2,2-dichloro-vinyl)-cyclopropane-1R-carboxylate], $R_f$=0.31 (in a 3:1 mixture of petroleum ether and ethyl acetate);

1β-hydroxy-2β-(but-2-cis-enyl)-3-methylene-cyclopentane-4β-yl-[2,2-dimethyl-3-(2,2-difluoro-vinyl)-cyclopropane-1-carboxylate]; this is an isomeric mixture containing a cis-trans acid component; $R_f$=0.34 (3:1 mixture of petroleum ether and ethyl acetate).

EXAMPLE 12

7.5 g. of 3,3aα,4,5,6,6aα-hexahydro-2-hydroxy-4α-chloromethyl-5β-yl-(+)-trans-chrysanthemate in 25 ml. of anhydrous benzene are reacted with 26.3 ml. of a 1 molar triphenyl-ethylidene-phosphorane solution (in benzene, 26.3 millimoles) in nitrogen atmosphere at 10° to 15° C. 100 ml. of benzene are added after half an hour, whereupon the mixture is extracted with 25 ml. of a saturated sodium chloride solution, dried over anhydrous sodium sulfate, filtered and evaporated in vacuo.

The crude product is subjected to chromatography on 150 g. of silica-gel; the eluting solvent is a 3:1 mixture of benzene and ethyl acetate. The fractions corresponding to an $R_f$ value of 0.56 (in a 4:1 mixture of petroleum ether and ethyl acetate) are collected and evaporated. Thus 7.28 g. (93.7%) of 1β-hydroxy-2β-(but-2-cis-enyl)-3α-chloromethyl-cyclopentane-4β-yl-(+)-trans-chrysanthemate are obtained. $R_f$=0.68 (in a 3:1 mixture of petroleum ether and ethyl acetate).

EXAMPLE 13

3 g. (0.85 millimoles) of 1β-hydroxy-2β-(but-2-cis-enyl)-3α-chloromethyl-cyclopentane-4-yl-(+)-trans-chrysanthemate are dissolved in 15 ml. of 1,5-diazabicyclo[4,3,0]-non-5-ene and the solution is stirred at 60° C. under argon for 5 hours. The suspension formed is cooled to room temperature and 150 ml. of ether are added. The organic layer is subsequently washed with two 50 ml.-portions of 0.1 N hydrochloric acid, 20 ml. of a 1% sodium hydrogen carbonate solution and 20 ml. of saturated sodium chloride solution, dried over anhydrous sodium sulfate, filtered and evaporated in vacuo. Thus 2.2 g. (81.6%) of 1β-hydroxy-2β-(but-2-cis-enyl)-3-methylene-cyclopentane-4β-yl-(+)-trans-chrysanthemate are obtained. The product is completely identical with the compound prepared according to Example 11.

EXAMPLE 14

In an analogous manner to Example 12 the following compound is prepared:

1β-hydroxy-2β-(but-2-cis-enyl)-3α-phenylthiomethyl-cyclopentane-4β-yl-(+)-trans-chrysanthemate; $R_f$=0.65 (in a 4:1 mixture of petroleum ether and ethyl acetate).

What we claim is:

1. An optically active or racemic compound of the formula I

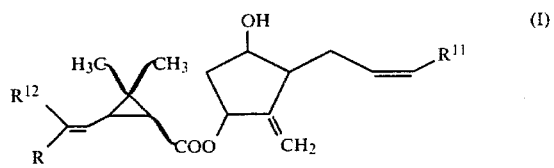

wherein
R$^{11}$ is a straight or branched chain lower alkyl or 1-alkenyl or hydrogen;
R and R$^{12}$ are the same or different and are hydrogen, halogen, straight or branched chain lower alkyl, or one of the moieties R and R$^{12}$ is lower alkoxycarbonyl;
the ~ bonds represent α- and/or β-configuration and the — bonds represent β-configuration.

2. A compound as defined in claim 1 wherein R$^{11}$ is hydrogen or lower alkyl or alkenyl; and R and R$^{12}$ are lower alkyl or halogen.

3. A compound as defined in claim 2 wherein R$^{11}$ is hydrogen, methyl, ethyl or vinyl and R and R$^{12}$ are methyl, chlorine, bromine or fluorine.

4. A compound selected from the group which consists of:

1β-hydroxy-2β-(but-2-cis-enyl)-3-methylene-cyclopentane-4β-yl-(+)-trans-chrysanthemate;

1β-hydroxy-2β-(pent-2-cis-enyl)-3-methylene-cyclopentane-4β-yl-(+)-trans-chrysanthemate;

1β-hydroxy-2β-(prop-2-enyl)-3-methylene-cyclopentane-4β-yl-(+)-trans-chrysanthemate;

1β-hydroxy-2β-(but-2-cis-enyl)-3-methylene-cyclopentane-4β-yl-{2,2-dimethyl-3S-(2,2-dichloro-vinyl)-cyclopropane-1-carboxylate}; and 1β-hydroxy-2β-(but-2-cis-enyl)-3-methylene-cyclopentane-4β-yl-{2,2-dimethyl-3-(2,2-difluoro-vinyl)-cyclopropane-1-carboxylate}.

5. An insecticidal composition comprising as active ingredient an effective amount of at least one compound of the formula I

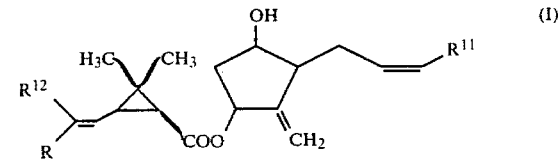

wherein
R$^{11}$ is a straight or branched chain lower alkyl or 1-alkenyl or hydrogen;
R and R$^{12}$ are the same or different and are hydrogen, halogen, straight or branched chain lower alkyl, or one of the moieties R and $R^{12}$ is lower alkoxycarbonyl;

the bonds represent α- and/or β-configuration and the — bonds represent β-configuration, in admixture with an inert solid, liquid or gaseous carrier.

6. An insecticidal composition comprising as active ingredient an effective amount of a compound as defined in claim 2.

7. An insecticidal method of treatment which comprises applying to an insect-infested host an effective amount of a compound as defined in claim 1 for a period sufficient to ameliorate the infestation.

* * * * *